(12) United States Patent
Termanini (10) Patent No.: US 9,861,485 B2
(45) Date of Patent: Jan. 9, 2018

(54) REVERSE KNEE PROSTHESIS

(71) Applicant: Zafer Termanini, Port St. Lucie, FL (US)

(72) Inventor: Zafer Termanini, Port St. Lucie, FL (US)

(73) Assignee: JOINT INNOVATION TECHNOLOGY, LLC, Boca Raton, FL (US)

( * ) Notice: Subject to any disclaimer, the term of this patent is extended or adjusted under 35 U.S.C. 154(b) by 0 days.

(21) Appl. No.: 15/024,369

(22) PCT Filed: Sep. 25, 2014

(86) PCT No.: PCT/US2014/057433
§ 371 (c)(1),
(2) Date: Mar. 24, 2016

(87) PCT Pub. No.: WO2015/048273
PCT Pub. Date: Apr. 2, 2015

(65) Prior Publication Data
US 2016/0235540 A1    Aug. 18, 2016

Related U.S. Application Data

(60) Provisional application No. 61/883,226, filed on Sep. 27, 2013.

(51) Int. Cl.
*A61F 2/24* (2006.01)
*A61F 2/38* (2006.01)
(Continued)

(52) U.S. Cl.
CPC ............. *A61F 2/38* (2013.01); *A61F 2/3854* (2013.01); *A61F 2/3886* (2013.01);
(Continued)

(58) Field of Classification Search
CPC ........ A61F 2/38; A61F 2/3836; A61F 2/3854; A61F 2/3886; A61F 2/4684
See application file for complete search history.

(56) References Cited

U.S. PATENT DOCUMENTS 3,694,821 A * 10/1972 Moritz .................. A61F 2/3854
 623/20.22
3,840,905 A    10/1974 Deane
(Continued)

FOREIGN PATENT DOCUMENTS

JP    2000107209 A    4/2000
JP    2000342610 A    12/2000

OTHER PUBLICATIONS

International Search Report for Application No. PCT/US2014/057433 dated Jan. 9, 2015.
(Continued)

*Primary Examiner* — Christopher D Prone
*Assistant Examiner* — Suba Ganesan
(74) *Attorney, Agent, or Firm* — Norris McLaughlin & Marcus PA (57) ABSTRACT

A reverse knee prosthesis for use in knee replacement surgery having a femoral component and a trochleal component. The femoral component comprises a stem, which is affixed in a femur, and a femoral cup having a generally concave portion which is sized to articulate on the trochleal component. The femoral cup also comprises a posterior lip and an anterior lip wherein the anterior lip is longer than the posterior lip. The trochleal component is affixed to a tibial tray which in turn is affixed to the tibia and has a transverse curved body with a narrowed waist. The generally concave portion of the femoral cup has a ridge extending outwardly therefrom, the ridge being sized to articulate on the narrowed waist.

20 Claims, 10 Drawing Sheets (51) Int. Cl.
  *A61F 2/46* (2006.01)
  *A61F 2/30* (2006.01)
(52) U.S. Cl.
  CPC ....... *A61F 2/4684* (2013.01); *A61F 2002/305* (2013.01); *A61F 2002/30301* (2013.01); *A61F 2002/30331* (2013.01); *A61F 2002/30387* (2013.01); *A61F 2002/30878* (2013.01); *A61F 2002/30884* (2013.01); *A61F 2002/30934* (2013.01)

(56) References Cited

U.S. PATENT DOCUMENTS

| | | | |
|---|---|---|---|
| 3,868,730 A | | 3/1975 | Kaufer et al. |
| 3,916,451 A | | 11/1975 | Buechel et al. |
| 4,134,158 A | * | 1/1979 | Laure .................... A61F 2/3845 623/20.24 |
| 4,224,696 A | | 9/1980 | Murray et al. |
| 4,249,270 A | | 2/1981 | Bahler et al. |
| 4,309,778 A | | 1/1982 | Buechel et al. |
| 4,470,158 A | | 9/1984 | Pappas et al. |
| 5,776,201 A | * | 7/1998 | Colleran ............... A61F 2/4684 623/20.31 |
| 6,117,175 A | * | 9/2000 | Bosredon .............. A61F 2/3854 623/20.22 |
| 6,197,064 B1 | | 3/2001 | Haines et al. |
| D473,307 S | | 4/2003 | Cooke |
| 6,726,724 B2 | | 4/2004 | Repicci |
| 7,141,053 B2 | | 11/2006 | Rosa et al. |
| 2004/0220675 A1 | | 11/2004 | Lewis et al. |

OTHER PUBLICATIONS

Written Opinion of the International Search Authority for Application No. PCT/US2014/057433 dated Jan. 9, 2015.
European Search Report for corresponding EP Application No. 14 847 813.4 dated Jan. 24, 2017.

* cited by examiner

REVERSE KNEE PROSTHESIS

CROSS-REFERENCE TO RELATED APPLICATION

This application is a 371 application of PCT/US2014/057433 filed Sep. 25, 2014, which claims priority benefit to U.S. provisional application Ser. No. 61/883,226 filed Sep. 27, 2013.

BACKGROUND OF THE INVENTION

Field of the Invention

The present invention relates generally to a knee resurfacing prosthesis and more specifically it relates to a knee implant prosthesis for knee resurfacing.

Description of the Related Art

It can be appreciated that knee-resurfacing prostheses have been in use for years to treat articulating surfaces destroyed by arthritis or pathological processes secondary to trauma. Basically, the natural knee joint comprises an upper femoral articulating surface having two condylar surfaces and a lower tibial plateau comprising two cupule shaped tibial condyles articulating smoothly with the upper femoral condyles. Typically, knee replacement prostheses are comprised of several types of prostheses, where articulating components of the knee are removed and replaced with metal and polyethylene components.

Prior art devices have attempted to duplicate the geometry of the natural articulating surface, where the femoral component has a semicircular C shaped design such as depicted in a U.S. Pat. No. 4,224,696. The bicondylar design is similarly disclosed in prior patents by F. Buechel and Pappas in U.S. Pat. Nos. 4,309,778 and 4,470,158. A more recent bicondylar design is described in U.S. Pat. No. D473,3075 and U.S. Pat. No. 6,197,064 B1. The prior art describes the bicondylar prosthesis as having a middle patellar groove for the femoral patellar articulation. Other knee implant devices are used to resurface only one femoral condyle such as unicondylar prostheses described in U.S. Pat. No. 7,141,053 and U.S. Pat. No. 6,726,724. Multiple designs of hinged implants also have been described basically for use in revision procedures and cases where bone loss and instability precluded the use of conventional implants. The design of the present invention is not a hinge. And, unlike hinged designs, my design allows the two articulating surfaces of the tibia and the femur to separate slightly in extreme ranges of motion such as squatting or during running.

In these respects, the reverse knee resurfacing prosthesis according to the present invention substantially departs from the conventional concepts and designs of the prior art, and in so doing provides an apparatus primarily developed for the purpose of resurfacing the articulating surfaces of the femur and the tibia using a reverse geometry where the femoral component has the shape of a cupule and the preferred embodiment of the tibial component has the shape of a trochlea, a cylinder or curved surface having a groove it its middle portion. In doing so, the reversed geometry provides significant advantages, both mechanical and anatomical, over previously known knee implants. The mechanical advantage being a significant increase in the contact surface between the tibia and the femur thereby reducing pressure forces and consequently reducing wear.

In previously known implants, the curved femoral implant surface contacts the flat tibial articulating surface with a very small surface area and, as a result, the pressure load can exceed three to four times the body weight. This stress concentration increases wear of the polyethylene tibial tray and reduces the efficacy and life of the implant. In my reverse knee implant, the contact surface encompasses the concave surface of the femoral cup, thereby distributing the pressure load over a large surface and minimizing wear. The anatomical advantage lies in the fact that my reverse geometry and anterior lip feature eliminates the need for cruciate ligaments. The shape of my femoral cup provides considerable stability in the anterior-posterior plane and prevents the femur from sliding forward. During the stance and swing phase of ambulation, the constraining geometry of the anterior and posterior lips of the femoral cup replace the mechanical effect of the anterior and posterior cruciate ligaments.

SUMMARY OF THE INVENTION

In view of the foregoing disadvantages inherent in knee resurfacing prostheses previously known in the art, the present invention provides a new reverse knee resurfacing prosthesis construction for use in knee resurfacing procedures. The prosthesis of the present invention provides increased ranges of motion and improved stability as well as a substantial reduction of wear.

BRIEF DESCRIPTION OF THE DRAWINGS

Various other objects, features and attendant advantages of the present invention will become fully appreciated as the same become better understood when considered in conjunction with the accompanying drawings, in which like reference characters designate the same or similar parts throughout the several views, and wherein.

DESCRIPTION OF THE PREFERRED EMBODIMENT

Figure 1:
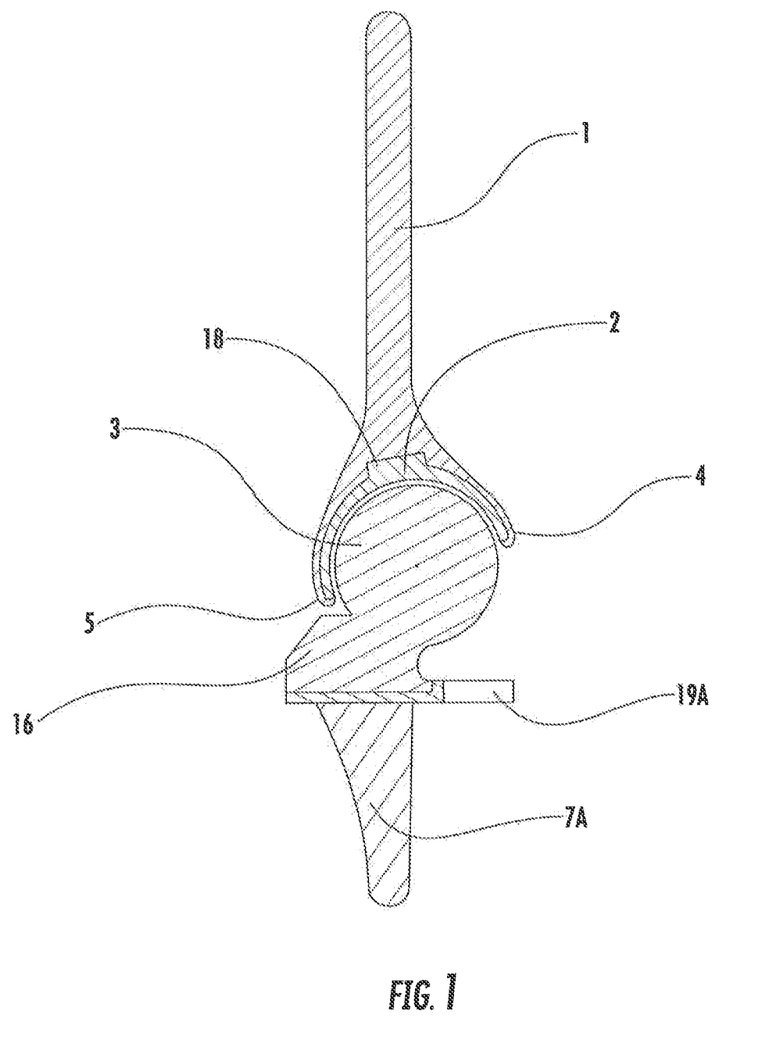
FIG. 1 is a side cross sectional view of the prosthesis.
Figure 1A:
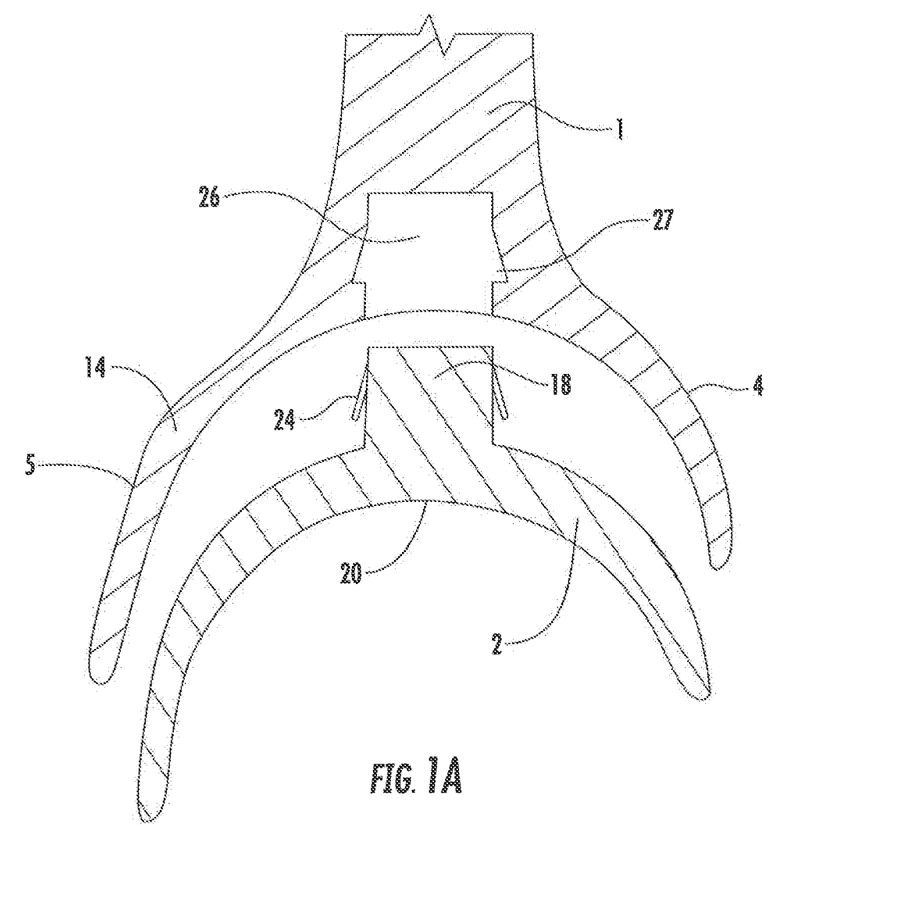
FIG. 1A is a partial exploded section view illustrating in detail the polyethylene liner and the femoral cup of FIG. 1.

Referring to the drawings, the present invention generally comprises a femoral component having a stem 1 or 1A to be inserted in and affixed in the femur and a femoral cup 14. A lining 2 or 2A in the form of a shell is secured onto the concave surface of the femoral cup 14. It is understood that the preferred lining is polyethylene but materials other than polyethylene can be used as the lining as is well known in the art. The lining comprises a ridge 20 oriented from the front to the back. The ridge 20 articulates in the central groove 21 of the trochleal component 3. It is secured to the cup by guide 18 and liner locking tabs 24. As illustrated in exploded section view 1A, guide 18 is sized to fit in recess 26. Recess 26 has locking liner recesses 27 in the side walls thereof. As guide 18 is pressed into recess 26, lining locking tabs 24 are pressed toward the side walls of guide 18 and they snap open into locking lining recesses 27 when guide 18 is fully pressed into recess 26, thereby locking lining 2 into femoral cup 14.

The femoral cup has a posterior lip 4 or 4A and an anterior lip 5. The anterior lip 5 must have a length longer than posterior lip 4 or 4A so that cruciate ligaments are unnecessary.

Figure 4:
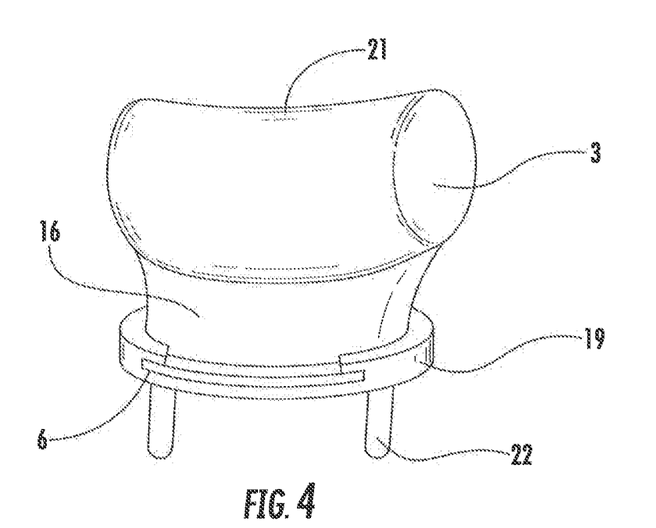
FIG. 4 is a frontal perspective view of the tibial component comprising a trochleal component and a tibial tray.
Figure 5:
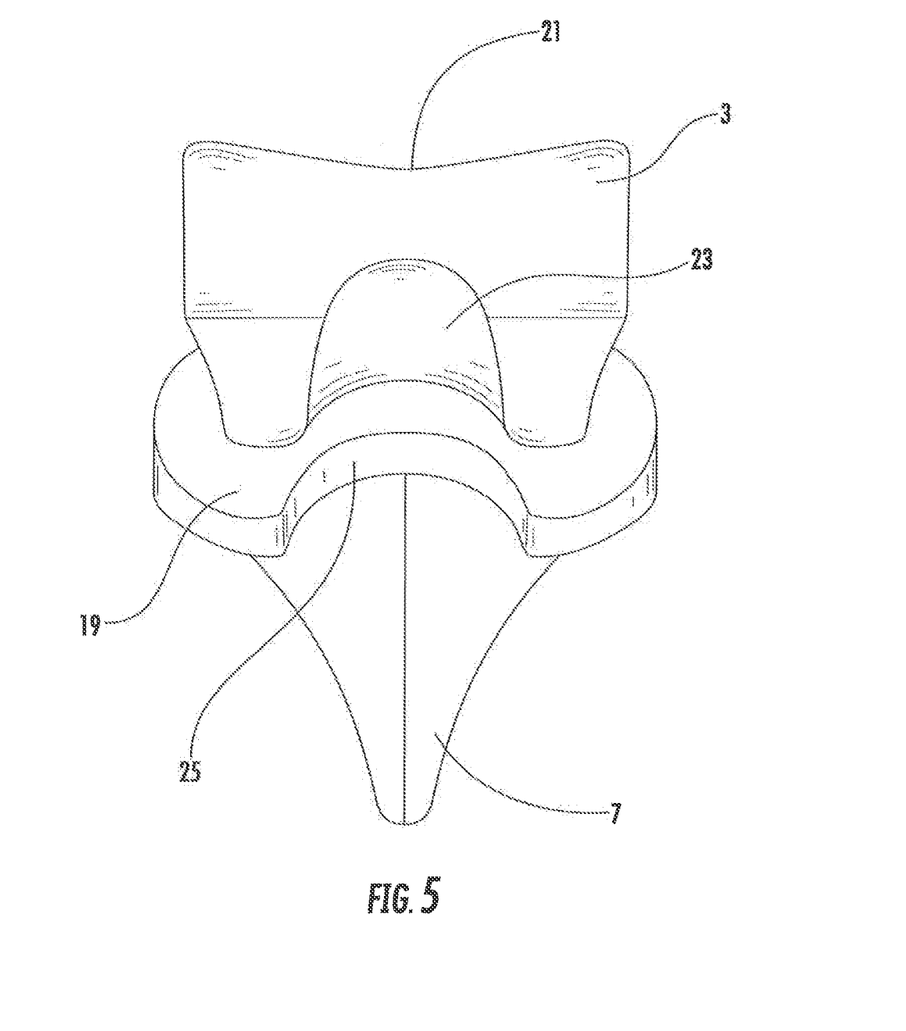
FIG. 5 is a rear view of the tibial component revealing the trochleal component and a posterior recess.
Figure 6:
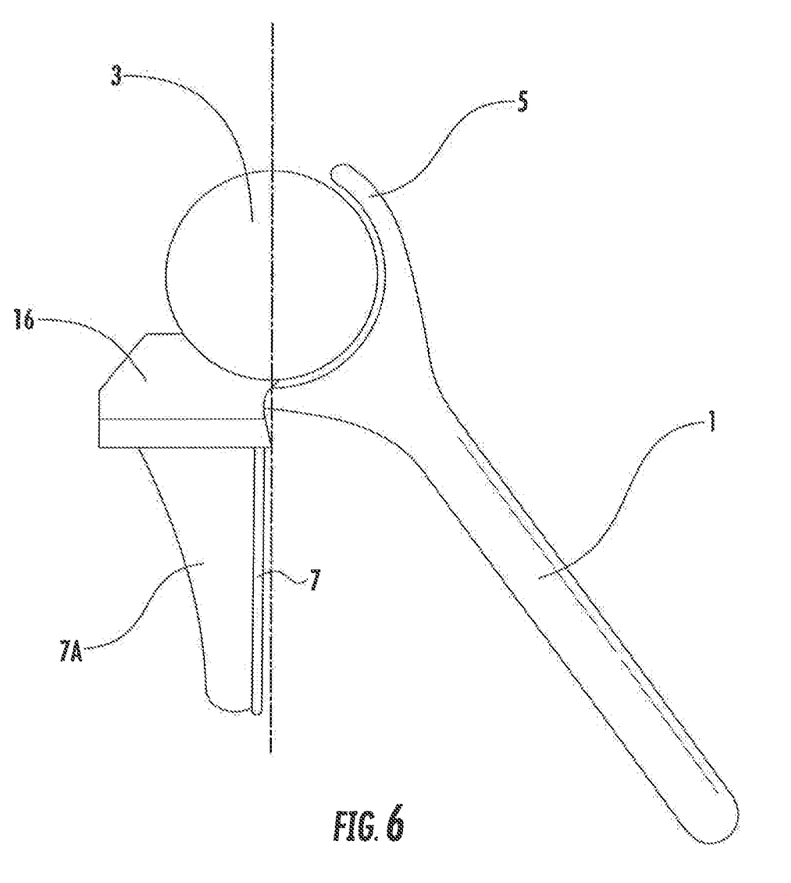
FIG. 6 is a side elevation view of the prosthesis wherein the posterior lip is situated in the posterior recess, allowing excessive flexion.

Referring to FIGS. 4 and 5, the trochleal component 3 has a transverse curved body with a narrowed waist 21. Said trochleal component 3 has a highly polished surface, which will allow articulation with the lined femoral cup. The trochleal component is attached to the tibial tray 19 or 19A by a neck 16. Posteriorly (FIG. 5), the neck 16 and trochleal component 3 provide a central posterior recess 23, which will receive the posterior lip 4 of the femoral cup during extreme flexion. (See FIG. 6.)

There are various ways to secure the tibial component to the tibia as will be apparent to those having skill in the art based upon the disclosures herein. Two tibial component embodiments are discussed herein. In FIG. 4, tibial tray 19 is provided with stabilizing posts 22 which are implanted in the tibia. In FIGS. 1, 2, 5 and 6, tibial tray 19A is provided with a stabilizing fin 7 having a rib 7A thereon which is implanted into the tibia. The tibial tray 19 or 19A can be further secured to the tibia using screws such as screw 31 illustrated in section in FIG. 4C.

The trochleal component 3 is secured to the tibial tray 19 after the tibial tray is secured to the tibia. This is accomplished by sliding the trochleal component 3 into a slotted portion of tibial tray 19 or 19A. The tibial tray has a tray locking tab 17 which functions in the same manner as lining locking tabs 24. When the trochleal component 3 is slid into the tibial tray, the tray locking tab 17 is pressed downwardly until slot 17A is positioned over the tray locking tab 17, then tab 17 pops up and locks trochleal component 3 in place.

Figure 4A:
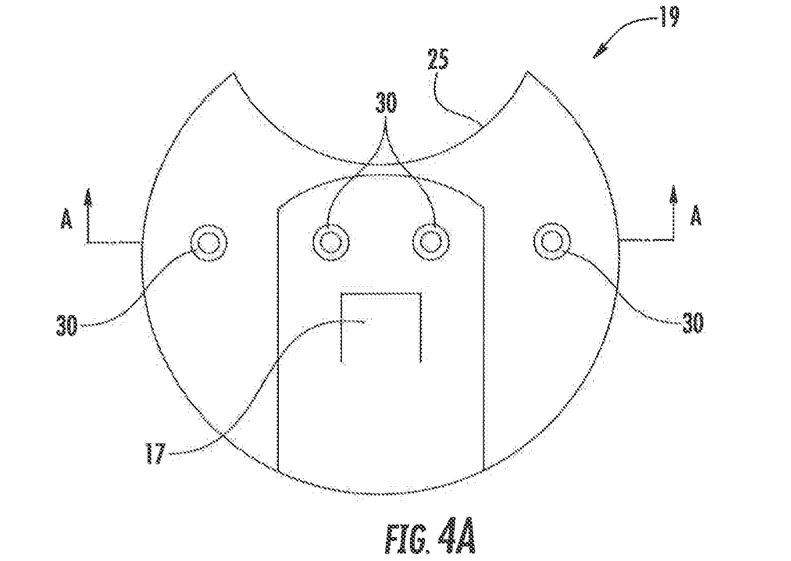
FIG. 4A is a top view of the tibial tray of FIG. 4.
Figure 4B:
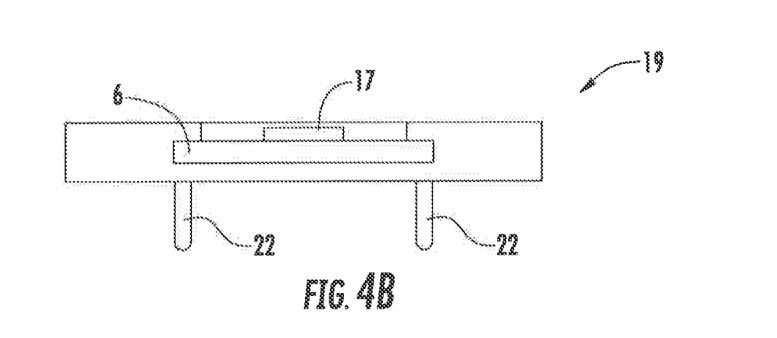
FIG. 4B is a frontal elevation view of FIG. 4A.
Figure 4C:
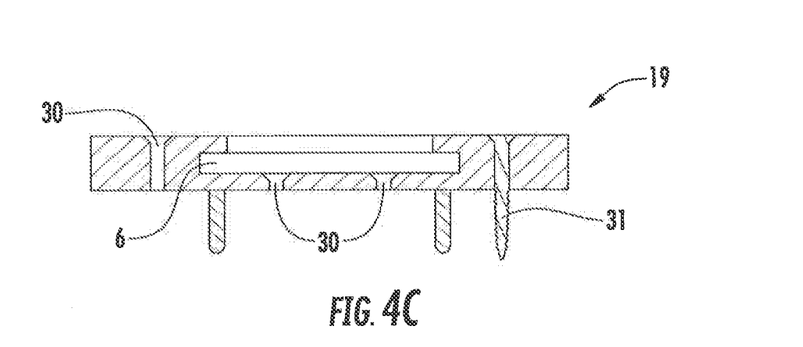
FIG. 4C is a section view taken along section line A-A of FIG. 4A.

FIGS. 4A, B and C illustrate the tibial tray 19 of FIG. 4 in more detail. This embodiment of tibial tray 19 comprises stabilizing posts 22 slotted portion 6, posterior notch 25 and optional screw holes 30. FIG. 4C illustrates a flat head screw 31 in section in one of the optional screw holes 30. The tibial tray can be affixed to the tibia by various means known in the art such as screws, pins, cement or various combinations thereof. The construction of the tibial tray 19 of FIG. 4 is the same as the construction of the tibial tray 19A of FIGS. 1, 2, 5 and 6 with the difference being that tibial tray 19A comprises stabilizing fin 7 and tibial tray 19 comprises stabilizing posts 22.

Figure 4D:
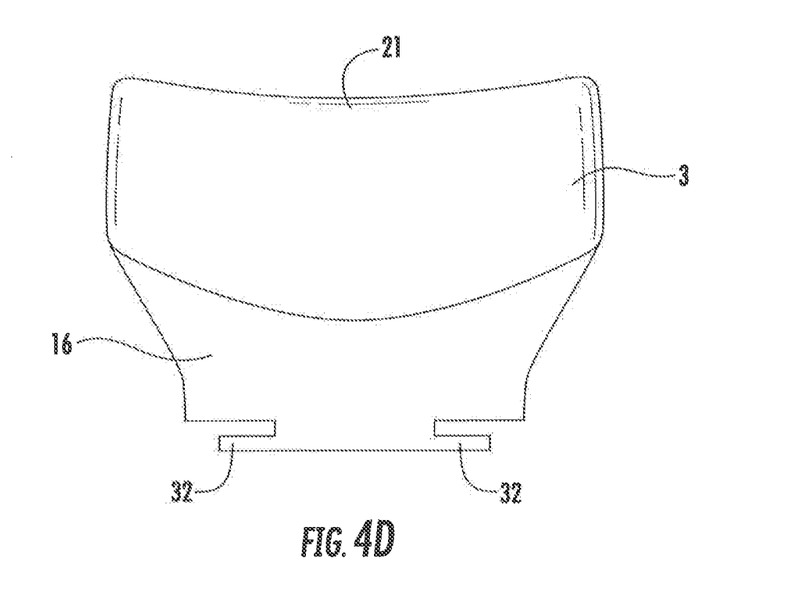
FIG. 4D is an elevation view of the trochleal component of FIG. 4 with an added section of a screw.
Figure 4E:
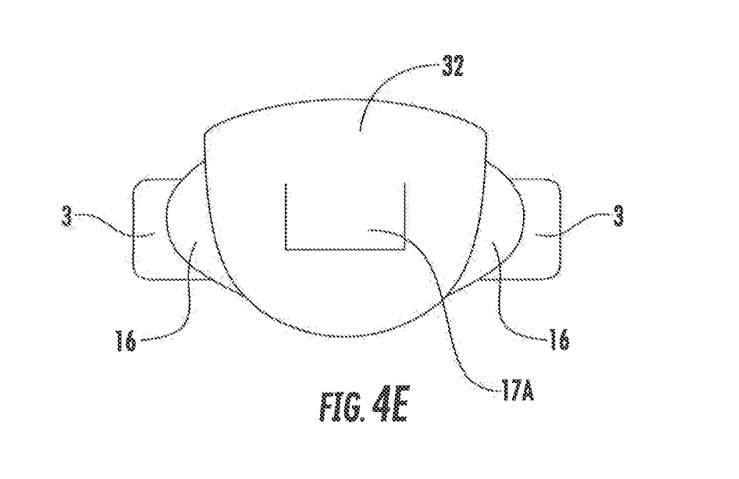
FIG. 4E is a bottom view of FIG. 4D.

FIG. 4D is an elevation view of the trochleal component 3 of FIG. 4. The trochleal component 3 comprises central groove 21, neck 16 and Tab 32. FIG. 4E is a bottom view of FIG. 4D. Trochleal component 3 is affixed to tibial tray 19 by sliding tab 32 into slot 6 and locking it in position as explained above.

The tibial tray 19 comprises a semi-circular notch 25 (FIGS. 4A and 5) to allow extreme flexion.

A kit containing the component parts of the knee replacement prosthesis of the present invention contains two or more trial plastic implants having different sizes and two or more prostheses of the invention having the same sizes as the trial plastic implants. Thus, the trial plastic implants each include a stem and femoral cup, a trochleal component and a tibial component. Two or more permanent linings of different thicknesses are also included in the kit along with two or more trial plastic linings, each trial plastic lining has a thickness corresponding to a permanent lining thickness. A permanent lining, such as a polyethylene lining, of appropriate thickness is selected during surgery using the trial implants and linings to make the best fit of the prosthesis to the patient. The construction of the trial plastic lining is different from the permanent lining in that guide 18 does not contain locking tabs 24. This allows the surgeon to test trial plastic linings of different thicknesses in each trial plastic implant.

In the surgical method for implanting the prosthesis of the invention, the surgeon will first make an anterior midline incision. Then the patella is dislocated laterally and the knee is flexed. The femur then is prepared first by inserting an intramedullary guide rod and then making appropriate distal femoral cuts using cutting guides. The tibia then is prepared by making appropriate cuts using a cutting guide. A trial plastic implant is then temporarily implanted in the patient and the trial plastic linings are tested. Then the range of motion of the knee is checked for stability. When the stability is satisfactory, the trial plastic implant components are removed and replaced with a permanent prosthesis and lining having the same sizes as the trial implant and lining. Thus, the tibial tray is affixed in place followed by affixing the femoral stem in the femur by impacting. While the knee is in flexion, the lining is locked in place. Then the trochleal component is affixed in the tibial tray. The patella may or may not need to be resurfaced depending on the degree of damage to its articular surface.

It is to be noted that the following are considered as alternatives to the foregoing embodiment that can be incorporated in conjunction or individually:

The tibial and femoral components can be made of metal such as titanium or a metallic alloy such as cobalt chrome. They can be also made of ceramic such as alumina or silicone nitride or the like, or other biocompatible materials having sufficient strength for the intended purpose.

Figure 2:
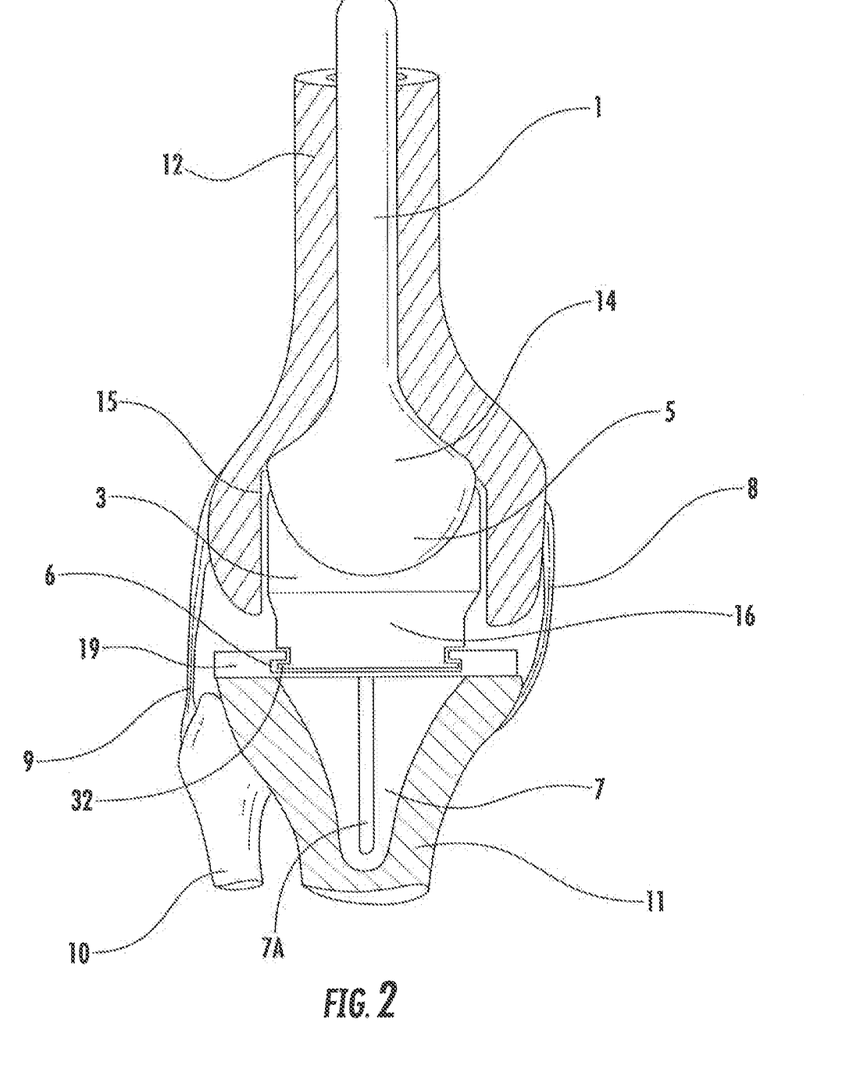
FIG. 2 is a front elevation view of the implanted prosthesis, illustrating the femur and tibia in section wherein the femoral component is seated in the femur and tibial component is seated in the tibia.
Figure 2A:
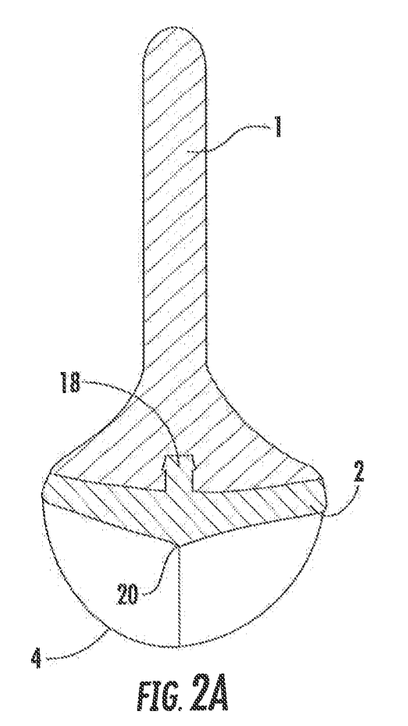
FIGS. 2A and 2B are section views of two embodiments of the femoral stem and femoral cup of FIG. 2.
Figure 2B:
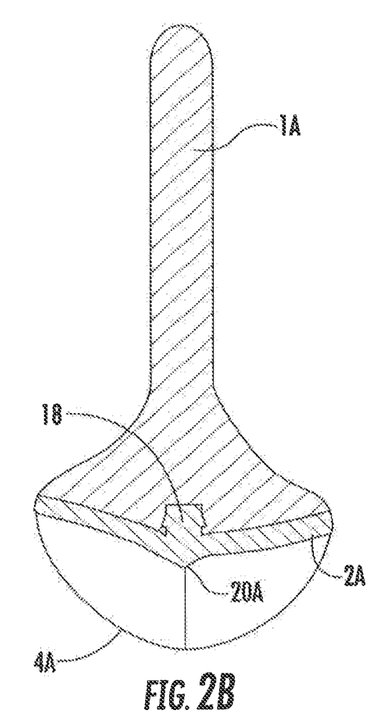
Figure 3:
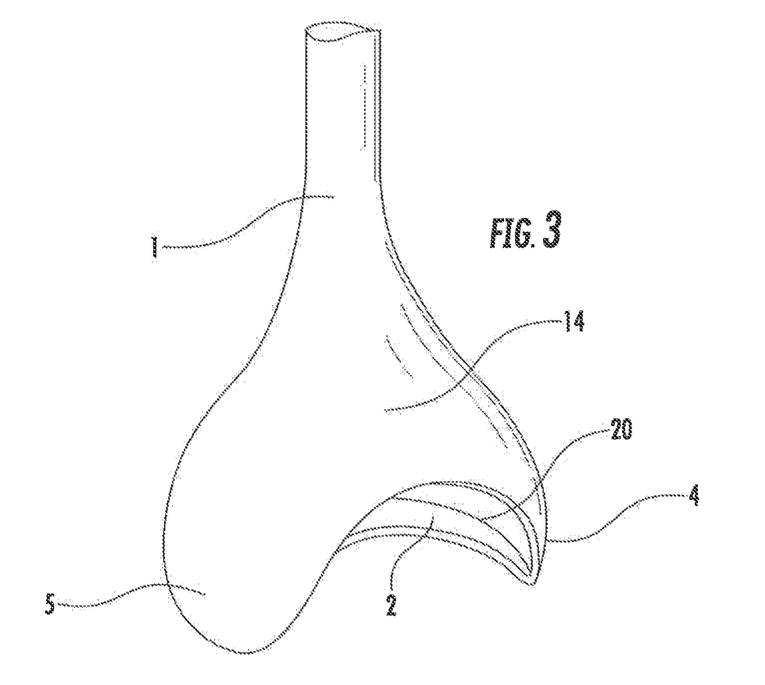
FIG. 3 is a perspective view of the femoral cup.

The trough 15 illustrated as in FIG. 2 is a space between the femur and the trochleal component 3. It can be made wider in order to allow some rotation of the trochlea vis a vis the femoral cup.

Figure 7:
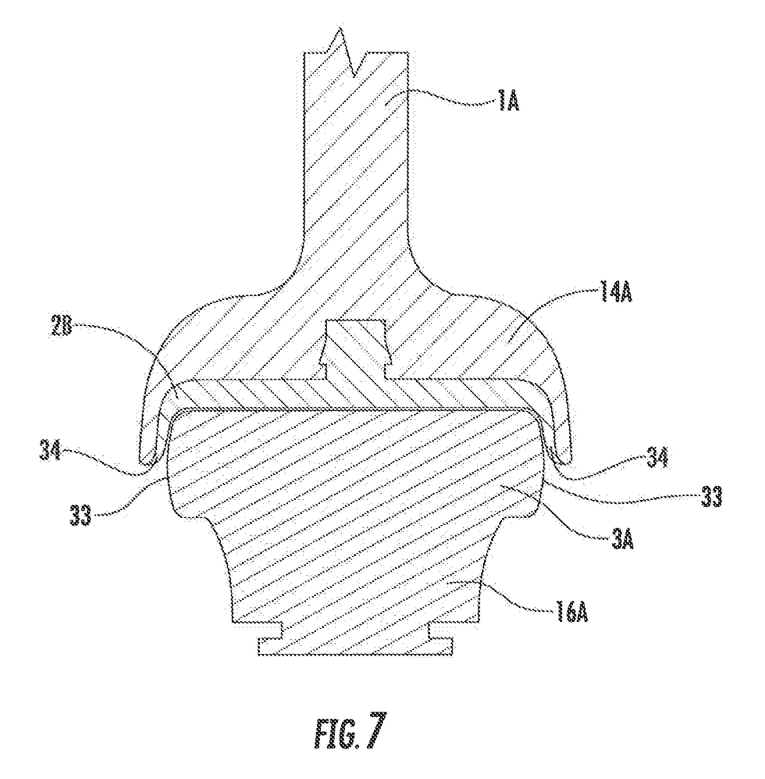
FIG. 7 is a section view of an alternative embodiment of the invention.

Instead of the tibial component having the shape of a trochlea, it can have a curved surface without a groove in its middle portion and the concave surface of the femoral cup will be shaped compatibly with structure to prevent undesired lateral movement. This embodiment is illustrated in section in FIG. 7. Stem 1A is the same as stem 1 of FIG. 1 but femoral cup 14A is different from femoral cup 14 because femoral cup 14A has side portions which extend over the ends of trochleal component 3A to limit lateral movement of the femoral cup relative to the trochleal component. Neck 16A is essentially of the same construction as neck 16. Polyethylene liner 2B articulates on the top of trochleal component 3A and the side portions 34 of polyethylene liner 2B can articulate on the ends 33 trochleal component 3A.

What is claimed is:

1. A knee prosthesis comprising
a femoral component having a femoral cup at a proximal end and a femoral stem at a distal end, the femoral cup comprising a concave surface sized for articulation on a trochleal component,
the trochleal component having a transverse curved body with a narrowed waist, the concave surface of the femoral cup having a ridge extending outwardly therefrom, the ridge of the femoral cup being sized to articulate on the narrowed waist of the transverse curved body, and
the femoral cup further comprising a posterior lip having a first length and an anterior lip having a second length wherein the second length of the anterior lip is longer than the first length of the posterior lip and the trochleal component further comprises a posterior recess which receives the posterior lip during extreme flexion.

2. The knee prosthesis of claim 1 wherein the femoral stem is adapted to be affixed to a femur and the trochleal component is affixed to a tibial tray that is adapted to be affixed to a tibia prior to being affixed to the trochleal component.

3. The knee prosthesis of claim 1 wherein the concave surface of the femoral cup has a lining affixed therein.

4. The knee prosthesis of claim 3 wherein the lining is comprised of polyethylene.

5. A surgical method for implanting the prosthesis of claim 1 in a patient comprising affixing the femoral stem in a femur and affixing the tibial tray to a tibia followed by affixing the trochleal component to the tibial tray.

6. The method of claim 5 further comprising affixing a lining in the concave surface of the femoral cup.

7. The method of claim 6 further comprising selecting a lining having a thickness that is the appropriate thickness for the patient and then affixing the selected liner into the femoral cup.

8. The surgical method of claim 5 wherein
a trial plastic implant is first implanted in a patient followed by inserting a trial plastic lining, then the knee is tested for stability,
repeating the foregoing step until stability is achieved, then removing the trial plastic implant and trial plastic lining and following the method of claim 5 using a permanent implant having the same size as the removed trial plastic implant and trial plastic lining.

9. The knee prosthesis of claim 1, wherein the curved body of the trochleal component has a circumference, a diameter and a total length defined between a first end and a second end, wherein the total length of the curved body is greater than the diameter of the curved body.

10. The knee prosthesis of claim 9, wherein the concave surface of the femoral cup is configured to articulate on a portion of the circumference of the curved body of the trochleal component.

11. The knee prosthesis of claim 9, wherein the narrowed waist of the curved body provides a central groove along the total length of the curved body between the first and second ends of the curved body, and further wherein the ridge extending outwardly therefrom the femoral cup is oriented from a front to a back of the femoral cup and is configured to articulate on the central groove of the curved body.

12. The knee prosthesis of claim 1, wherein a portion of the curved body of the trochleal component comprises the posterior recess that receives the posterior lip of the femoral cup during extreme flexion.

13. A kit adapted for use in knee replacement surgery comprising
two or more trial plastic femoral components of different sizes, each having a femoral cup at a proximal end and a femoral stem at a distal end, each femoral cup comprising a concave surface sized for articulation on a trochleal component,
two or more trial plastic trochleal components of different sizes, each having a transverse curved body with a narrowed waist, the concave surface of the femoral cup having a ridge extending outwardly therefrom, the ridge being sized to articulate on the narrowed waist,
the femoral cup further comprising a posterior lip having a first length and an anterior lip having a second length wherein the second length is longer than the first length and each trochleal component further comprises a posterior recess which receives the posterior lip during extreme flexion,
two or more trial plastic linings having different thicknesses, and
one or more trial plastic tibial tray,
and further comprising two or more knee prostheses of claim 1, each knee prosthesis of claim 1 having a size corresponding with a size of a trial plastic implant, and
two or more linings, each having a thickness corresponding with a thickness of a trial plastic lining.

14. A knee prosthesis comprising:
a femoral component having a femoral cup at a proximal end and a femoral stem at a distal end, the femoral cup comprising a concave surface configured for articulation on a trochleal component, and,
the trochleal component having a transverse curved body with a narrowed waist and two ends the concave surface of the femoral cup having a ridge extending outwardly therefrom, the ridge of the femoral cup being sized to articulate on the narrowed waist of the transverse curved body, and wherein the femoral component comprises side portions sized to extend over only a part of the two ends of the trochleal component,
the femoral cup further comprising a posterior lip having a first length and an anterior lip having a second length wherein the second length of the anterior lip is longer than the first length of the posterior lip and the trochleal component further comprises a posterior recess which receives the posterior lip during extreme flexion.

15. The knee prosthesis of claim 14 wherein the femoral stem is adapted to be affixed to a femur and the trochleal cup is affixed to a tibial tray that is adapted to be affixed to a tibia prior to being firmly affixed to the trochleal component of the knee prosthesis.

16. The knee prosthesis of claim 14 wherein the concave surface of the femoral cup has a lining affixed therein.

17. The knee prosthesis of claim 16 wherein the lining is comprised of polyethylene.

18. The knee prosthesis of claim 14, wherein the curved body of the trochleal component has a circumference, a diameter and a total length defined between a first end and a second end, wherein the total length of the curved body is greater than the diameter of the curved body.

19. The knee prosthesis of claim 18, wherein the first end of the curved body comprises a first end surface and the second end of the curved body comprises a second end surface, and further wherein the side portions of the femoral cup overlap only portions of the first and second end surfaces of the curved body of the trochleal component.

20. The knee prosthesis of claim 14, wherein a portion of the curved body of the trochleal component comprises the posterior recess that receives the posterior lip of the femoral cup during extreme flexion.

* * * * *